US00PP33382P2

(12) United States Plant Patent
O'Connell

(10) Patent No.: US PP33,382 P2
(45) Date of Patent: Aug. 17, 2021

(54) ***GRAPTOSEDUM* PLANT NAMED 'SUNSPLASH'**

(50) Latin Name: ***Graptosedum* hybrid**
Varietal Denomination: SUNSPLASH

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 16/873,315

(22) Filed: Mar. 17, 2020

(51) Int. Cl.
*A01H 5/02* (2018.01)
*A01H 6/32* (2018.01)

(52) U.S. Cl.
USPC ..... Plt./479
CPC ..... *A01H 6/328* (2018.05); *A01H 6/32* (2018.05)

(58) Field of Classification Search
USPC ..... Plt./479, 373
CPC ..... A01H 5/12; A01H 5/02
See application file for complete search history.

*Primary Examiner* — Kent L Bell
(74) *Attorney, Agent, or Firm* — Cassandra Bright

(57) ABSTRACT

A new and distinct cultivar of *Graptosedum* plant named 'Sunsplash' is disclosed, characterized by milky lemon yellow leaves, with a blush of greyed-purple. The new cultivar branches freely, and grows at a moderate rate, quickly filling the pot for commercial nurseries. The new variety is a *Graptosedum*, typically produced as a container plant for the patio or as landscape plants, as well as a variety of ornamental purposes.

3 Drawing Sheets

Latin name of the genus and species: *Graptosedum* hybrid.

Variety denomination: 'SUNSPLASH'.

BACKGROUND OF THE INVENTION

The new cultivar, *Graptosedum* 'SUNSPLASH', is the product of a planned breeding program. The new variety originated as a naturally occurring whole plant mutation of the proprietary, unpatented, seed parent, *Graptosedum* 'California Sunset'. The new cultivar 'SUNSPLASH' was discovered by the inventor, Renee O'Connell, in March 2017, in Vista, Calif., at a commercial greenhouse.

Asexual reproduction of the new cultivar 'SUNSPLASH' was first performed May 2017 in Vista, Calif., at a commercial greenhouse, by terminal vegetative cuttings. *Graptosedum* 'SUNSPLASH' has since asexually produced multiple generations and has shown that the unique features of this cultivar are stable and reproduced true to type.

SUMMARY OF THE INVENTION

The cultivar 'SUNSPLASH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUNSPLASH'. These characteristics in combination distinguish 'SUNSPLASH' as a new and distinct *Graptosedum* cultivar:

1. *Graptosedum* 'Sunsplash' exhibits milky lemon yellow leaves, with a greyed-purple blush.
2. *Graptosedum* 'Sunsplash' due to its unusual milky lemon yellow color, provides a great accent for dish garden centerpieces for the table or patio.

3. *Graptosedum* 'Sunsplash' branches freely, and grows at a moderate rate, quickly filling the pot for commercial nurseries.

PARENTAL COMPARISON

Plants of the new cultivar are similar to plants of the parent, in most horticultural characteristics, however, plants of the new cultivar differ in the following;

1. *Graptosedum* 'Sunsplash' exhibits milky lemon yellow leaves whereas *Graptosedum* 'California Sunset' produces blue green to rose mauve leaves.

COMMERCIAL COMPARISON

The new cultivar 'Sunsplash' can be compared to the unpatented commercial variety *Graptosedum* 'Blue Giant'. Plants of the *Graptosedum* 'Blue Giant' are similar to plants of the new cultivar 'Sunsplash' in most horticultural characteristics. However, the new cultivar 'Sunsplash' differs in the following:

1. *Graptosedum* 'Sunsplash' produces leaves of milky lemon yellow, blushed greyed-purple, whereas *Graptosedum* 'Blue Giant' produces baby blue leaves.
2. *Graptosedum* 'Sunsplash' exhibits a faster rate of growth than does *Graptosedum* 'Blue Giant'.
3. *Graptosedum* 'Sunsplash' eventually produces a plant cluster measuring 2 feet or more in diameter, whereas the cluster of *Graptosedum* 'Blue Giant' is approximately 12 inches in diameter.

The new cultivar 'Sunsplash' can be compared to the unpatented commercial variety *Graptosedum* 'Vera Higgins'. Plants of *Graptosedum* 'Vera Higgins' are similar to plants of the new cultivar 'Sunsplash' in most horticultural characteristics. However, plants of the new cultivar 'Sunsplash' differ in the following:

1. *Graptosedum* 'Sunsplash' produces fleshy, glabrous leaves, whereas *Graptosedum* 'Vera Higgins' produces leaves that are more rounded, with pruinose epidermis.
2. *Graptosedum* 'Vera Higgins' displays rosettes of whitish aqua leaves, whereas *Graptosedum* 'Sunsplash' produces leaves of milky lemon yellow, blushed greyed-purple.
3. *Graptosedum* 'Sunsplash' grows faster than *Graptosedum* 'Vera Higgins'.

BRIEF DESCRIPTION OF THE PHOTOGRAPHS

The accompanying photograph in FIG. 1 illustrates in full color a typical plant of 'SUNSPLASH' grown in a greenhouse in Vista, Calif. (approximately 2300 foot candles).

Figure 1:
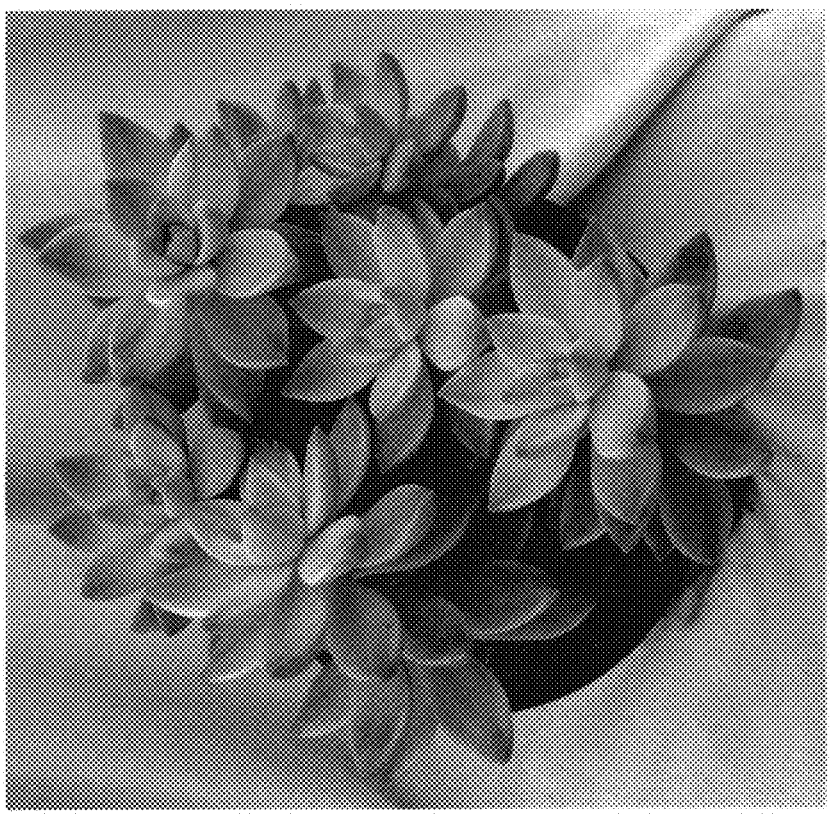
Figure 2:
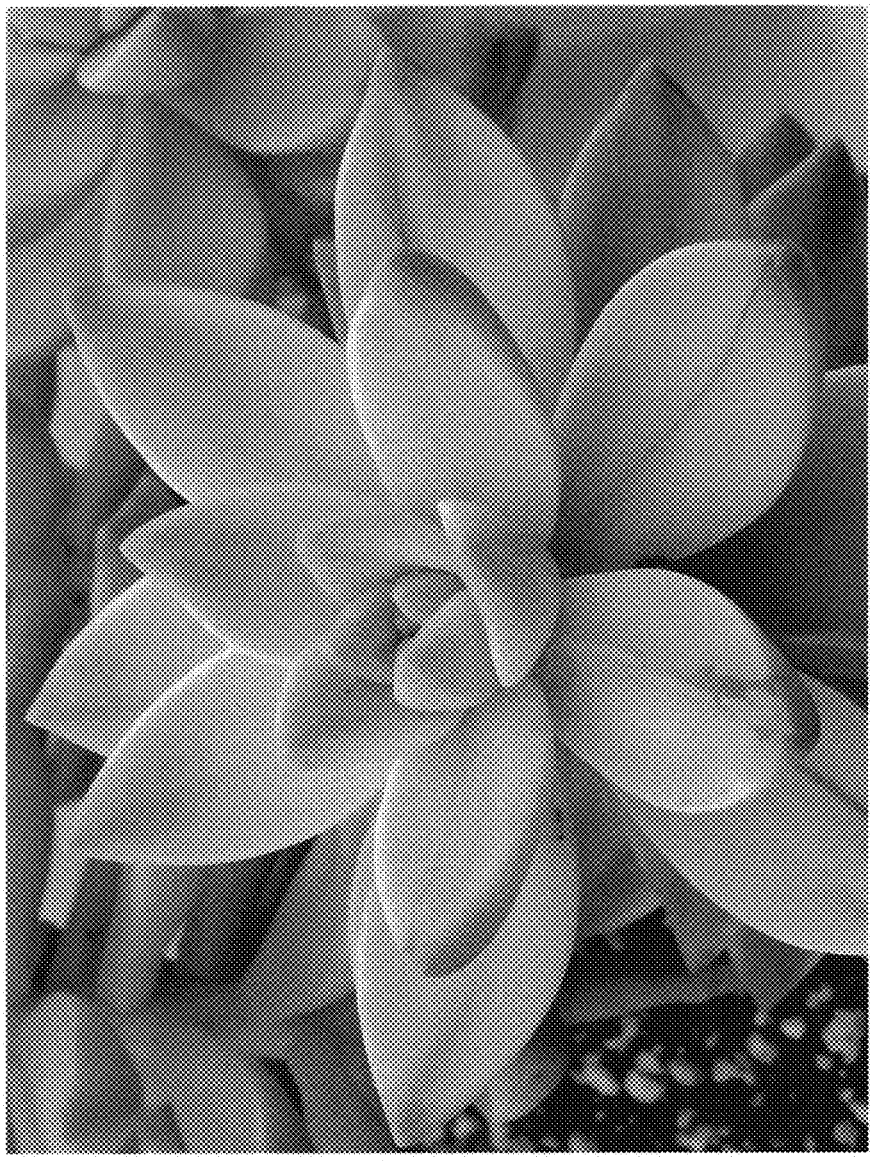
FIG. 2 illustrates a close up of the foliage.
Figure 3:
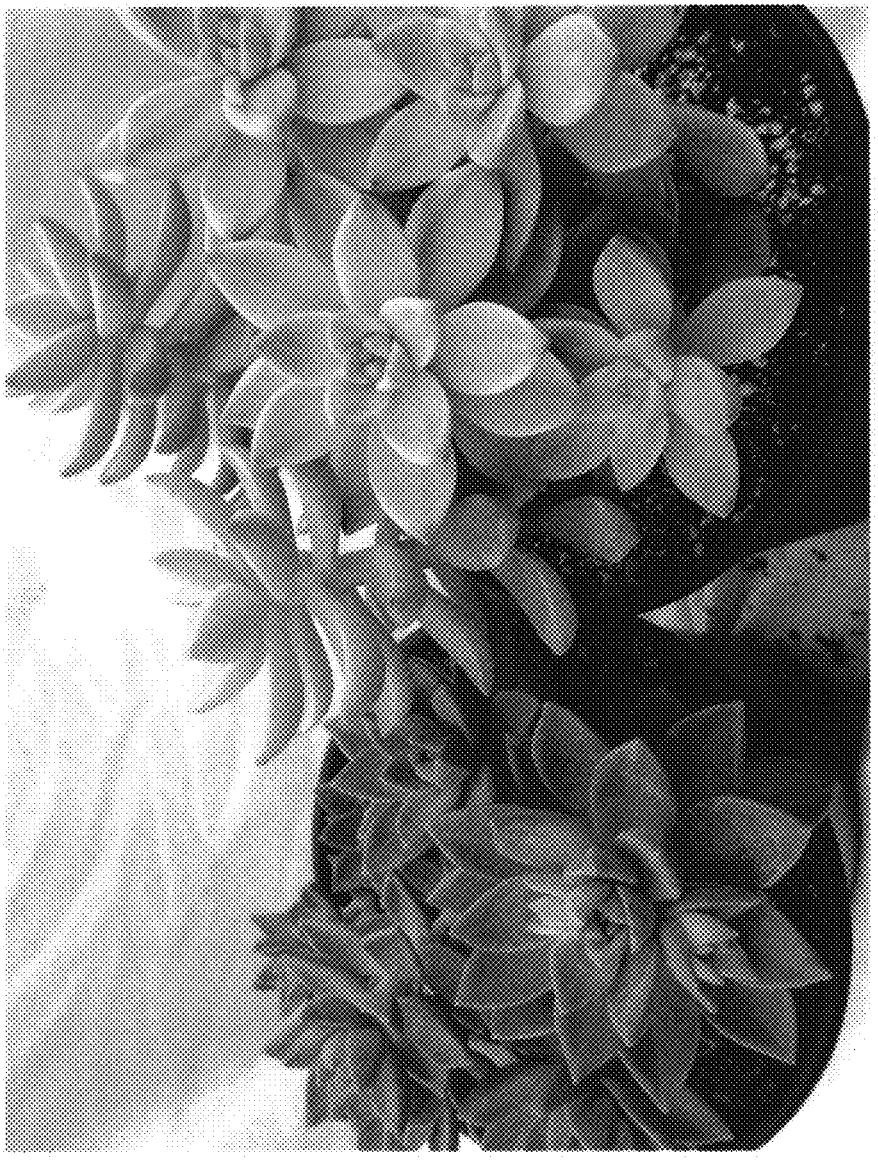
FIG. 3 illustrates the new variety 'SUNSPLASH' on the right, on the left is the unpatented *Graptosedum* 'California Sunset'.

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Graptosedum* plant. Temperatures ranged from −1° C. to 29° C. night and day. No artificial light, photoperiodic treatments or chemical treatments were given to the plants. Plants are approximately 8 months old.

DETAILED BOTANICAL DESCRIPTION

In the following description, color references are made to The Royal Horticultural Society Colour Chart, except where general terms of ordinary dictionary significance are used. The following observations and measurements describe 'Sunsplash' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 fc of light. Measurements and numerical values represent averages of typical plant types.

Botanical classification: *Graptosedum* hybrid 'SUNSPLASH'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 1 gallon.

Growth habit: Upright branching sub-shrub.

Height: Approximately 15 cm to top of highest leaf.

Plant spread: Approximately 22 cm. Plant comprised of 6 main stems.

Growth rate: Moderately fast.

Branching characteristics: Moderate branching from a pinch.

Stem:

*Length*.—About 10 to 12 cm.

*Diameter*.—About 8 mm.

*Texture*.—Glabrous.

*Color*.—Near RHS Yellow-Green 145C.

*Internode*.—About 5 mm.

FOLIAGE

Arrangement: Whorled.

Average length: 3-4 cm.

Average width: 1.5 cm.

Width at base: Average 5 mm.

Aspect of leaf: Slight upward curve.

Leaf thickness: 8-9 mm.

Shape of blade: Oblate to nearly spatulate.

Apex: Mucronate.

Base: Attenuate.

Margin: Entire.

Texture of top surface: Glabrous.

Texture of bottom surface: Glabrous.

Quantity of leaves per plant: Approximately 20 to 30 per stem.

Color:

*Young foliage upper side*.—Near RHS Yellow-Green 145D. Center 145B, apex flushed Greyed-Purple N186C.

*Young foliage under side*.—Near RHS Yellow-Green 145D. Center 145B, apex flushed Greyed-Purple N186C.

*Mature foliage upper side*.—Base near RHS Yellow-Green 145C. Center 145B, upper 30 to 50% flushed Greyed-Purple N186C.

*Mature foliage, under side*.—Near RHS Yellow-Green 145B, base 145C. apex 138B lightly flushed Greyed-Purple N186C.

Venation: Parallel. Color same as leaf blade.

FLOWER

Not observed.

REPRODUCTIVE ORGANS

Not observed.

OTHER CHARACTERISTICS

Fruits and seeds: Not observed.

Temperature tolerance: Tolerates temperatures from approximately 0° C. to at least 32° C.

Disease/pest resistance: Neither resistance or susceptibility to normal diseases and pests of *Graptosedum* has been observed.

Drought tolerance: Tolerates at least 2 weeks of high temperatures without supplemental water, showing no serious damage to plant.

What is claimed is:

1. A new and distinct cultivar of *Graptosedum* plant named 'SUNSPLASH' as herein illustrated and described.

* * * * *